United States Patent [19]
Milne et al.

[11] Patent Number: 5,958,463
[45] Date of Patent: Sep. 28, 1999

[54] AGRICULTURAL PESTICIDE FORMULATIONS

[75] Inventors: Christopher G. Milne, Greenback; Paulus P. Shelby, Jr., Knoxville, both of Tenn.

[73] Assignee: Agri-Tek, Inc., Greenback, Tenn.

[21] Appl. No.: 08/754,859

[22] Filed: Nov. 22, 1996

Related U.S. Application Data

[63] Continuation-in-part of application No. 08/248,480, May 24, 1994, abandoned, which is a continuation of application No. 08/067,530, May 23, 1993, abandoned, which is a continuation of application No. 07/737,202, Jul. 29, 1991, abandoned.

[51] Int. Cl.$^6$ .......................... A01N 25/00; A01N 55/08; A01N 59/14; A01N 9/127
[52] U.S. Cl. .......................... 424/660; 424/405; 424/450; 424/600; 424/613; 424/615; 424/617; 424/657; 424/658; 424/659; 424/195.1; 514/64; 514/77; 514/78; 514/78.3; 514/937; 514/964; 514/972; 514/975; 504/122; 504/187; 504/193; 71/DIG. 1
[58] Field of Search .......................... 424/657, 658, 424/659, 660, 405, 450, 600, 617, 613, 615, 195.1; 514/78, 783, 64, 77, 937, 964, 972, 975; 71/DIG. 1; 504/187, 193, 122

[56] References Cited

U.S. PATENT DOCUMENTS

| | | |
|---|---|---|
| 360,700 | 4/1887 | Kaatz et al. . |
| 496,110 | 4/1893 | Brown . |
| 890,636 | 6/1908 | Fride . |
| 907,498 | 12/1908 | Hicks . |
| 1,029,203 | 6/1912 | Leowenthal . |
| 1,635,461 | 7/1927 | Cramer . |
| 1,757,222 | 5/1930 | Schepss et al. . |
| 1,911,551 | 5/1933 | Cleveland . |
| 1,923,004 | 8/1933 | Seitz . |
| 1,976,905 | 10/1934 | Thodarson . |
| 2,711,367 | 6/1955 | Parish . |
| 2,770,538 | 11/1956 | Vierling . |
| 2,773,757 | 12/1956 | Correll et al. . |
| 2,968,590 | 1/1961 | Ploquin . |
| 3,007,844 | 11/1961 | Schulz . |
| 3,009,598 | 7/1961 | Brikner . |
| 3,012,931 | 12/1961 | Sokoloff . |
| 3,305,298 | 2/1967 | Chapman . |
| 3,531,278 | 9/1970 | Nies . |
| 3,560,381 | 2/1971 | Winters et al. . |
| 3,674,458 | 7/1972 | Schattner . |
| 3,706,161 | 12/1972 | Jenson . |
| 3,873,700 | 3/1975 | Misato et al. ............... 514/78 |
| 4,291,497 | 9/1981 | Manankov . |
| 4,303,726 | 12/1981 | Turner . |
| 4,363,798 | 12/1982 | D'Orazio . |
| 4,400,298 | 8/1983 | Boocock et al. . |
| 4,610,881 | 9/1986 | Bechgaard . |
| 4,661,157 | 4/1987 | Beauford et al. . |
| 4,666,747 | 5/1987 | Quinn ................... 106/15.05 |
| 4,681,617 | 7/1987 | Ghyczy et al. ............ 71/DIG. 1 |
| 4,721,706 | 1/1988 | Bessler et al. ............ 514/78 |
| 4,855,090 | 8/1989 | Wallach . |
| 4,873,084 | 10/1989 | Sallay . |
| 4,944,950 | 7/1990 | Sakharova . |
| 4,959,221 | 9/1990 | Holmes . |
| 4,996,053 | 2/1991 | Hatcher . |
| 5,019,312 | 5/1991 | Wallach . |
| 5,077,057 | 12/1991 | Szoka, Jr. ............... 424/450 |
| 5,098,483 | 3/1992 | Tsudo et al. . |
| 5,104,664 | 4/1992 | Palmere et al. . |
| 5,225,278 | 7/1993 | Kielbania . |
| 5,225,279 | 7/1993 | Redlich . |
| 5,229,366 | 7/1993 | Chaudhuri et al. . |
| 5,256,181 | 10/1993 | Manalastas et al. . |
| 5,269,979 | 12/1993 | Fountain . |
| 5,277,914 | 1/1994 | Szoka . |
| 5,310,496 | 5/1994 | Taylor et al. . |
| 5,310,721 | 5/1994 | Lo . |
| 5,317,004 | 5/1994 | Misselbrook et al. . |
| 5,332,584 | 7/1994 | Scher et al. . |
| 5,460,816 | 10/1995 | Palmere et al. . |
| 5,464,613 | 11/1995 | Barcay . |
| 5,525,147 | 6/1996 | Palmere et al. . |
| 5,648,532 | 7/1997 | Hawthorne et al. ............ 564/8 |
| 5,888,473 | 3/1999 | Hawthorne et al. ............ 424/1.21 |

OTHER PUBLICATIONS

Litchtenberg, Lipsomes: Preparation, Characterization and Preservation,: *Methods of Biochemical Analysis*, 1988, pp. 337–462, vol. 33, J. Wiley & Sons, NY.

Edited by Gregoriadis, G. and Allison, A.C., *Liposomes in Biological Systems*, 1980, pp. 101–151, John Wiley & sons, NY.

Edited by Poznanski, M. and Juliano, R., *Pharmaceutical Reviews*, 1984, pp. 277–335, vol. 36, No. 4, The American Society for Pharmacology and Experimental Therapeutics, U.S.A.

Edited by Miyamoto, J. and Hearney, P., "Physicochemical Properties of Formulations . . ." *Pesticide Chemistry Human welfare and the Environment*, 1983, pp. 257–269, vol. 4, Pergamon Press, NY.

Dijkstra et al., Chemical Abstracts, vol. 114, #97796, 1991.

Kirk–Othmer Encyclopedia of Chemical Technology, 4th ed., John Wiley & Sons, New York, 1995, vol. 15, pp. 192–210.

*Primary Examiner*—John Pak
*Attorney, Agent, or Firm*—Neil F. Markva

[57] ABSTRACT

The present invention relates generally to the method for the production of liposomal microencapsulated boron-containing products to be used for agricultural formulations. More specifically, a new method of production of liposomal microencapsulated is disclosed for active agents such as pesticides. A lecithin is mixed with an organic solvent in a certain proportion so as to provide solutions with varied levels of solubilized lecithin. The particular solvent being used will depend on the amount of active agent (AA) desired in the final solution. The formulation of the lecithin/organic solvent mixture is then allowed to settle. After settling, the top layer is separated and saved, while the bottom layer is discarded. An AA is then added to form a concentrate that is added to water for vesicle formation. Boron-containing materials formulated according to the invention may now be applied to agricultural field crops and fruits.

15 Claims, No Drawings

AGRICULTURAL PESTICIDE FORMULATIONS

This is a continuation-in-part application of application Ser. No. 08/248,480 filed May 24, 1994 now abandoned, which is a continuation of Ser. No. 08/067,530 filed May 23, 1993 now abandoned, which is a continuation of Ser. No. 07/737,202 filed Jul. 29, 1991 now abandoned.

FIELD OF THE INVENTION

The present invention relates generally to agricultural pesticides. More specifically, the invention relates to natural pesticides and the method of preparing them for efficacious use in protecting agricultural crops in the field.

BACKGROUND OF THE INVENTION

Boron-containing compounds including borates, boric acids, and boric oxides are well known for use as antiseptics pesticidal, and preservative uses. U.S. Pat. No. 1,911,551 is directed to an insect repellant and the following U.S. Patents are directed to various types of boron-containing materials used for destroying household insects such as ants, cockroaches, termites, and the like.

| | | | |
|---|---|---|---|
| 496,110 | 1,757,222 | 4,944,950 | 4,996,053 |
| 1,029,203 | 4,363,798 | 4,959,221 | 5,464,613 |

U.S. Pat. Nos. 1,635,461 and 2,968,590 disclose the use of boron-containing compounds to preserve fruit after harvesting and prevent the growth of fungus.

U.S. Pat. Nos. 360,700; 890,636; 907,498; 1,923,004; 1,976,905; and 3,012,931 show the use of various types of boron-containing materials for protecting plant vegetation such as trees by destroying insects and fungus that would adversely effect the foliage, flower, and fruit.

Japanese Patent Application No. 57[1982] - 47,903 and the following U.S. patents disclose the use of boron-containing compounds as wood preservatives before and after harvesting.

| | | | |
|---|---|---|---|
| 3,007,844 | 4,303,726 | 4,661,157 | 5,104,664 |
| 3,009,598 | 4,400,298 | 4,873,084 | 5,460,816 |
| 3,305,298 | 4,610,881 | 5,098,483 | 5,525,147 |
| 3,706,161 | | | |

U.S. Pat. No. 4,291,497 discloses the application of boron as a trace element in powder form onto plants being treated.

U.S. Pat. Nos. 711,367; 2,773,757; 3,531,278; and 3,560,381 show various types of boron-containing compositions used as herbicides. U.S. Pat. Nos. 2,770,538 and 3,674,458 show the use of boron-containing compounds as fertilizers.

As is known, the use of boron-containing materials as herbicides and insecticides for plant vegetation is very critical. Boron toxicity in agricultural use constitutes an important agricultural problem because natural soils may contain too much boron or be irrigated with water containing excessive concentrations of the element or boron fertilizers that are applied in excessive amounts. The management of soils regarding the amount of boron is difficult because the range between the deficient and toxic level of the element is known to be narrow. On the one hand, boron-containing compounds are useful on plants as insecticides to preserve vegetation. However, if too much boron is applied to the plant, it will be damaged. This is particularly a problem in products such as tobacco where the leaf itself is the product being harvested.

In the article "Some Considerations About the Tolerance of Various Plant Species to Excessive Supplies of Boron", *Soil Science*, 92:243–247 (1961), researchers J. J. Oertli and H. C. Kohl of the University of California examine the time necessary to produce boron toxicity symptoms with ten parts per million (ppm) in solution, and boron concentrations in leaves of various plant species. This article is incorporated herein in its entirety by reference to explain the known factors related to this fundamental problem in handling boron-containing materials such as borates.

Boron-containing pesticides are not for general use in the agricultural industry on field crops because no viable delivery system exists that will provide pesticidal characteristics without adversely affecting the leaf. In addition, available delivery systems do not maintain the pesticide in contact with the vegetation long enough to provide pesticidal effectiveness over an extended period of time. These problems are particularly true of insecticides. Environmental conditions such as the amount of rainfall, volatilization of the active ingredient, and wind conditions all adversely effect the potential use of boron-containing compounds for general agricultural use.

Various known delivery systems for pesticides in powder, solid, and liquid forms include liquid formulations such as emulsions, colloidal suspensions, organic and aqueous solutions containing the borons as shown in the various U.S. patents referenced herein. The following U.S. patents show various delivery systems used for pesticides.

| | | |
|---|---|---|
| 3,585,022 | 5,174,804 | 5,256,181 |
| 4,943,307 | 5,250,499 | 5,435,821 |

U.S. Pat. Nos. 5,526,181 and 5,435,821 disclose controlled or slow release formulations having active chemical agents coated with polymers including encapsulated boron-containing micronutrient. Basic problems relate to polymer encapsulation of agricultural fertilizers and pesticides, however. Moreover, nothing in these patents show the use of boron-containing compounds as pesticides and more specifically, as insecticides.

Commercially Available Pesticides

Other commercially known pesticides such as herbicides, fungicides, insecticides, bactericides and other active agents and compounds are applied periodically in the home, agriculture, and other places and can be dangerous to humans. Farmers, however, still need to spray their crops and animals with these active agents and compounds. To this end, there have been several unsuccessful attempts to provide a method of delivering these compounds in a manner that is safe, effective, and economical, as well as environmentally acceptable.

Various encapsulating techniques have been tried with agricultural active agents with results considered insufficient to justify replacement of existing agricultural formulations. Nothing in the prior art either suggests, teaches, or discloses the use of liposomal microencapsulation techniques to active agents such as pesticides in agricultural formulations.

Liposomal microencapsulation is known in the pharmaceutical industry and has five steps. Ethanol (95%) is mixed in a particular proportion with high grade soybean lecithin containing 50% phosphatidylcholine (PC). The ethanol soybean lecithin mixture is agitated until the PC and other soluble portions of the lecithin have been dissolved into the ethanol. The mixture is then allowed to stand for a period of time, so that the insoluble portions can settle to the bottom of the container, and the top becomes a clear amber color. The top portion is then drawn off and saved. The bottom sludge is discarded. A certain amount of water is added to the mixture, followed by a predetermined amount of ethanol.

The steps followed up to this point result in a basic "stock" solution that is mixed with an active agent (AA) of choice in the pharmaceutical industry. The next step is the addition of a preselected AA to the stock solution. The final step is to then add the preselected AA solution to water, thereby effecting formation of the microcapsules or vesicles.

This known pharmaceutical method is limited to the use of 95% ethanol as a solvent and a high grade (50% PC) granular soybean lecithin as the only lipid source. This procedure produces a dilute solution of lecithin because of the low amount of lecithin used and the addition of extra ethanol and water. This is acceptable in the medical field because dose rates are very low, thus requiring low loading potentials. This known process is not acceptable in other fields, however, which require higher loading potentials such as in agricultural formulations used for pesticides.

Ethanol is the only solvent that is usable in the pharmaceutical industry and that is a problem in many agricultural applications, because not all agricultural compounds are soluble in ethanol. Furthermore, ethanol is a highly flammable solvent, and expensive EPA regulations on the proper packaging of flammable materials make ethanol impractical to use in most agricultural uses necessitating a less flammable solvent system. For these reasons, there is no suggestion in the pharmaceutical use of ethanol to use ethanol in agricultural formulations.

The mere extraction of lecithin from animal sources such as egg yolks does not relate to the agricultural industry. Japanese Patent No. C87-154187 discloses the extraction of lecithin from egg yolks. It states that the uses and advantages are for food, drugs and toiletries. Japanese Patent Nos. C88-116693 and C89-086119 disclose methods of further extraction and purification of phosphatidylcholine (PC) from egg lecithin. These patents disclose the use of egg lecithin as an emulsifier for food, drugs, and toiletries, but do not suggest making liposomes or liposomal carrier systems. These Japanese patent references specify a method of extraction and purification of PC from egg lecithin.

As determined in the pharmaceutical industry, animal or egg lecithin contains a higher percentage of saturated fatty acid side chains, which impart a more rigid gelatinous quality to resulting liposomes when used for liposomal encapsulation of drugs. In turn, there is a slower, more extended release rate of the entrapped drugs. This characteristic is advantageous for drug delivery systems but is not desirable in agricultural applications of pesticides where there may be a risk of causing chemical residue problems.

The average price for high purity (99%) animal PC at $75.00 per 100 milligrams is $340,194.00 per pound. The average price for high purity (99%) egg PC at $76.00 per 100 milligrams is $34,473.00 per pound. Low purity (60%) PC egg PC at $0.68 per 100 milligrams is $308.44 per pound. Soybean lecithin with PC content between twenty percent (20%) to forty percent (40%) can be purchased for under $10.00 per pound.

Canadian Patent No. 834,472 discloses the process of extracting PC from crude vegetable oils using monoglycerides to aid the process. This reference discloses varying the levels of the monoglycerides and different ways of using the monoglycerides in the process. The reference does not mention, suggest, teach, or disclose liposome formation or, more specifically, liposomal encapsulation of active agents for agricultural uses. Its use is strictly for food additives, bakery uses, cosmetics, and a one word mention of a medical use.

Active agents of particular interest in the agricultural industry are pesticides, which is a generic term for herbicides, fungicides, bactericides, and insecticides. Other agricultural active agents include dyes and stains. It has been discovered in this invention that the key to encapsulating such active agents for agricultural applications is the amphipathic material known as lecithin and, more specifically, plant lecithin.

Plant Lecithin

In the American Oil Chemists' Society book entitled *Lecithins* and edited by Bernard F. Szuhaj and Gary R. List, at page 289, author Y. Pomeranz states that the "term 'lecithin' is the commercial or popular name for a naturally occurring mixture of similar compounds more accurately identified as phosphatides or phospholipids. The principal components of the natural mixture are phosphatidylcholine, phosphatidylethanolamine, inositol phosphatides and related phosphorus-containing lipids."

At page 1 of the book, *Lecithins*, author C. R. Scholfield says that "[I]n modern usage, lecithin generally refers to a complex, naturally occurring mixture to phosphatides obtained by water-washing crude vegetable oil and separating and drying the hydrated gums. In addition to the phosphatides, such products contain triglycerides and other substances that are removed in an emulsion with gums. Soybean lecithin, the most common commercial product, has been reported to contain 25–35% triglycerides and smaller amounts of other nonphosphatide materials."

Commercially available plant lecithin is composed of the phospholipids called phosphatidylcholine (PC), phosphatidylethanolamine (PE), phosphatidylinositol (PI), and phosphatidic acid (PA), carotenoid, and, depending on the grade of the plant lecithin, varying levels of oils, triglycerides, fibrous materials and, in some cases, additives and surfactants. Commercial lecithins are available in dry granular, liquid, gel, paste, and powder forms.

The invention is limited to the use of plant lecithins as contrasted with animal lecithins that are obtained from animal sources such as egg yolks. As is well known, plant lecithins are found in soybean oil, cottonseed oil, canola oil, wheat oil, kelp, peanuts, and sunflower seeds.

At pages 185–188 and 195 of the book *Lecithins* published in 1985, authors J. C. Schmidt and F. T. Orthoefer discuss nonfood uses of lecithin. A known miscellaneous function of lecithin is as a liposomal encapsulating agent. Among nonfood applications, however, lecithin is used as a liposomal encapsulating agent only in the pharmaceutical industry. The authors discuss agricultural and agriproduct processing uses of lecithin with a particular small section concerning pesticides.

Nothing in the book, *Lecithins*, teaches, discloses, or suggests the use of plant lecithin as the key to using liposomal encapsulating techniques for encapsulation of active agents such as pesticides for agricultural applications. Moreover, there is nothing in any prior art to suggest, teach, or disclose the liposomal encapsulation of active agents for agricultural applications.

It is known that pharmaceuticals and drugs are applied in low doses such as in milligrams and parts per million for human consumption. In comparison, pesticides are applied in known quantities measured in terms of pounds of active agent per acre of crop. All commercially available agricultural chemicals such as pesticides have known formulations for effecting their desired results. Some known pesticides contain as much a 48% and even up to 72% active agent in their known formulations.

The pharmaceutical application of lecithin, consequently, does not offer any help in using plant lecithin as a liposomal encapsulating agent in agricultural applications that require loading high concentrations of active agent into the initial stock solution composition of the invention. For example, the initial stock solution used in pharmaceutical applications uses a very low lipid content so that large amounts of active agent cannot be loaded into it.

It is known that PC is the material in plant lecithin that actually does the encapsulating in the liposomal microencapsulation process. The molecule of PC has a phosphate head with a choline moiety and some fatty acid chains that form a tail portion. The fatty acid chains are nonpolar and therefore repel water. The phosphate head of the PC molecule attracts water. When placed in water, the molecules coalesce so that the molecule tails are directed one way and the heads another to produce the vesicle formation of the liposomal encapsulation technique.

PURPOSE OF THE INVENTION

The primary object of the invention is to provide a delivery system for pesticidal amounts of boron-containing materials to field crops and fruits while precluding adverse effects of the boron on the crops and fruits.

Another primary object of the invention is to provide a method of liposomal microencapsulation that will lead to EPA and FDA approval of encapsulated active agents such as pesticides, which are readily available at low cost.

Another object is to provide an excellent protective barrier for pesticides and other active agents from ultraviolet radiation, thereby enhancing the active life of ultraviolet-degradable active agents in agricultural uses.

A further object is to provide a method that will encapsulate more active ingredient per unit of volume than is available in any liposomal encapsulation of the prior art.

Another object of the invention is to provide a safe delivery system of pesticides for agricultural uses that does not require specialized handling and storage facilities.

A still further object of the invention is to provide an encapsulation method that will produce an encapsulated product having a slow release of the encapsulated compound.

Another object of is to produce an encapsulated active agent that gives protection against microbial breakdown if the active agent is applied to the soil and that allows for the delivery of the active agent, which will not be removed by rain or irrigation.

Another object of the present invention is to provide a process of liposomal microencapsulation that requires fewer and more cost effective ingredients and is, therefore, less expensive and time consuming to produce.

A further object of the present invention is to provide a method of encapsulation that produces an encapsulated active agent, which binds the vesicles to the organic fraction of the soil thereby reducing leaching or runoff.

Another object of the present invention is to provide an encapsulator having better adhesion to plant cuticular waxes thereby preventing removal caused by rain or irrigation.

Still another object of the present invention is to reduce acute residue levels expected in plant tissue.

SUMMARY OF THE INVENTION

As disclosed and described herein, the novel agricultural pesticide formulations necessarily include a lecithin-saturated stock solution, an intermediated agricultural pesticide stock solution, and a liposomal encapsulated agricultural pesticide that includes a lipid vesicle having phospholipid materials derived from plant lecithin as its lipid source. Each of the methods for forming these novel agricultural pesticide formulations are part of a process of liposomal encapsulation of an agricultural pesticide.

Contrary to prior art teachings exemplified by U.S. Pat. Nos. 4,855,090 and 5,019,392, the invention uses organic solvents and phospholipid materials to produce encapsulated agricultural pesticides having new and unexpected inherent characteristics. The unique pesticide formulations of the invention control the growth of or destroy agricultural pests while inherently overcoming existing problems associated with agricultural pesticides. The pests include weeds, insects, fungi, and bacteria that are brought into contact with an effective amount of the encapsulated agricultural formulation of the invention for controlling the growth of or destroying such agricultural pests. Furthermore, the encapsulated agricultural pesticides of the invention unexpectedly maintain pesticidal efficacy while requiring ½ the number of field applications. Moreover, the problems of pesticide runoff, leaching, and volatilization unexpectedly are effectively curbed.

The invention is directed to preselecting a particular active agent such as a pesticide and an organic solvent for carrying the active agent. The same organic solvent must be effective to solubilize a plant lecithin to a lecithin-saturated level.

According to the invention, a plant lecithin is mixed with an organic solvent that is selected because it also dissolves the preselected active agent. The lecithin is present in a certain proportion so as to provide a solution with varied levels of lecithin saturation. In other words, an effective amount of lecithin is mixed in the organic solvent to form a saturated solution of lecithin. And it is well known that different organic solvents necessarily dissolve differing amounts of lecithin because of their varied levels of lecithin saturation from one organic solvent to the other.

The lecithin-saturation level will be dependent upon the amount of active agent (AA) desired in the final solution. That is, the organic solvent selected for dissolving the lecithin at its saturation level will also be effective to dissolve and otherwise carry the particular amount of AA desired in the final solution to be mixed with water to produce the vesicle formation.

Depending on the formulation of organic solvent and lecithin, the lecithin/organic solvent mixture is then allowed to settle. That is, when the formulation produces a mixture having a saturated solution of lecithin and undissolved portions of the lecithin, the undissolved portions are allowed to settle to the bottom of the mixture leaving the solution at its lecithin-saturation level of the organic solvent.

After settling, the top layer of lecithin-saturated solution of the lecithin/organic solvent mixture is separated and saved, while the bottom layer is discarded. The lecithin-saturated solution is called the "initial stock solution" for the purpose of describing this invention. An AA is then added to the stock solution and the resulting concentrate is added to water for the agricultural application.

The resulting concentrate is an intermediate active agent solution and includes the lecithin-saturated solution plus the amount of AA required to be used in the prior art as a pesticide in the subsequent agricultural application. The invention includes dissolving a plant lecithin to a saturation level in the organic solvent thereby producing the desired initial predetermined lecithin-saturated stock solution to be later mixed with the pesticide to be solubilized.

The invention is directed to a method for preparing an intermediate active agent solution containing a preselected active agent and being effective to produce liposomal microencapsulation of the active agent by mixing the intermediate active agent solution with water.

An organic solvent solution is selected that is capable of carrying the preselected active agent in the solvent solution in an amount sufficient for agricultural applications.

The organic solvent solution is also capable of dissolving a preselected plant lecithin in an amount sufficient to produce in the solution an amount of phosphatidylcholine effective to encapsulate the pesticide when the intermediate pesticide solution is mixed with water. The preselected plant lecithin is mixed with the organic solvent solution to produce an initial predetermined lecithin stock solution containing the desired amounts of phosphatidylcholine in the organic solvent solution.

The predetermined lecithin stock solution produced in said process mixing step is isolated and then at the desired time, mixed with an amount of the preselected active agent to form the intermediate active agent solution having an active agent content sufficient for agricultural uses. The intermediate active agent solution is mixed with water forming an agricultural liquid formulation having the active agent encapsulated in a liposomal composition.

A particular feature of the invention is directed to the use of a pesticide mixed with a solution having a w/v or v/v ratio of lecithin to organic solvent in the solvent solution of 1:1 or 1:2. The method is limited to the use of a plant lecithin. In a specific embodiment, the organic solvent solution includes N-methyl pyrrolidone and the plant lecithin has a phosphatidylcholine content in the range of from 5% to 50% of the lecithin.

More specifically, the invention is directed to a slow-release pesticide composite formulation comprising a boron-containing pesticide material in an amount sufficient to control pest which have a deleterious effect on agricultural crops. A slow release carrier material is bound to the boron-containing pesticidal material to release the pesticide material at a rate effective to provide pesticidal activity for protecting an agricultural crop without adversely effecting that crop. A specific feature of the invention is that the boron-containing material is a borate such as disodium octaborate tetrahydrate. The total amount of the boron-containing pesticidal material present in the formulation is sufficient to be otherwise toxic to the crop if the slow release carrying material were not bound to the pesticidal material. More specifically, the boron-containing pesticidal material is effective to destroy plant-eating insects located on agricultural plant crops.

Another feature of the invention is directed to a prepackaged boron product comprising a boron-containing material including a form of pesticidal boron in sufficient amounts to destroy plant-eating insects when the prepackaged boron product is mixed with water and sprayed onto agricultural plant crops. The boron-containing material is mixed in an organic solvent solution having a saturation level amount of plant lecithin in solution. The prepackaged boron product is effective to form a slow release pesticide composite formulation when mixed with water. A feature of the invention is directed to the use of disodium octoborate tetrahydrate in an amount sufficient to form a concentration of about 2 lbs of disodium octoborate tetrahydrate in each gallon of the boron product. The organic solvent used with the disodium octoborate tetrahydrate is ethylene glycol and includes a surfactant. The pesticidal boron is in a weight to weight ratio in a range of 500 parts per million to 2.5 lbs in each gallon of the boron product. The boron-containing material includes an effective amount of an insecticidal boron-based on an elemental boron content of up to about 5.5% by weight.

More particularly, the invention is directed to a pesticidal formulation that includes a boron-containing material selected from the group comprising: boric oxide, metaboric acid, sodium borate, disodium octaborate, disodium octaborate tetrahydrate, boron trioxide, anhydrous boric acid, borax, borax pentahydrate, borax decahydrate, a mixture of borax and boric acid, boric acid, sodium metaborate, sodium perborate, sodium tetraborate pentahydrate, sodium pentaborate, sodium pentaborate with anhydrous borax, potassium tetraborate, potassium pentaborate, ammonium biborate, ammonium pentaborate, an organometallic compound of boron, calcium boride, ulextile, colemanite, barium triborate, or calcium triborate.

The pesticidal material is an alkali metal borate or an alkaline earth metal borate or an alkali metal borohydride. The organic solvent solution includes carotenoid in an amount sufficient to control the ultraviolet degradability of the slow release pesticide composite when the formulation is disposed on vegetation. The organic solvent solution includes an organic solvent selected from the group of acetone, 100% denatured anhydrous ethanol, dimethylformamide, gamma butyrolactone, methylene chloride, and N-methyl pyrrolidone. The plant lecithin is derived from soybean oil, cotton seed oil, canola oil, wheat oil, kelp, peanut oil, or sunflower seed oil. The plant lecithin has a phosphatidylcholine content in the range of from about 5% to about 50%.

In another embodiment, the pesticidal material is selected from the group of alachlor, alphamethrin, atrazine, carbaryl, chlorothalonil, cymiazole, cupric hydroxide, cypermethrin, S-ethyl dipropylthiocarbamate, fluometuron, lambda cyhalothrin, permethrin, piperonyl butoxide, streptomycin, malathion, and trifluralin.

A method of the invention includes a method for controlling the growth of or destroying agricultural pests including weeds, insects, fungi, and bacteria comprising the step of bringing into contact with the agricultural pest an effective amount of pesticidal formulation having an organic-solvent solution with a saturation level amount of plant lecithin and a pesticidal material to be mixed with water to control the growth of or destroy an agricultural pest.

DETAILED DESCRIPTION

The present application discloses a method of delivering an active agent onto plants, animals, structure surfaces, soils, and the like. The active agent is microencapsulated liposomally, thereby providing a delivery mechanism and a controlled release mechanism for the active agent.

In the present process, a plant lecithin is mixed with an organic solvent in a certain proportion so as to provide a solution at a desired lecithin-saturation level depending on the formulation. The amounts of a particular form of plant lecithin required to obtain a desired level of solubility in certain organic solvents are known to the skilled artisan. The lecithin/organic solvent mixture is then allowed to settle. After settling, the top layer is separated and saved, while the bottom layer is discarded. An AA is then added to this stock solution and the resulting concentrate is added to water for the particular agricultural application. The concentrate must be added to water for vesicle formation.

Although, in the present invention, 100% denatured anhydrous ethanol may be used, it is only one of many solvents that can be used depending on the particular application.

known pesticides. In other words, the known agricultural use rate necessarily defines an amount of active agent sufficient for agricultural applications.

TABLE I

| COMMON NAME | AGRICULTURAL USE RATE (lb/A) | SOLVENT |
|---|---|---|
| Herbicides: | | |
| Alachlor | 1.5–8 | Soluble in ether, acetone, benzene, chloroform, ethanol, ethyl acetate, slightly soluble in heptane. |
| Atrazine | 2–4 | Dimethyl sulfoxide (18.3%), chloroform (5.2%), ethyl acetate (2.8%), methanol (1.8%), diethylether (1.2%), n-pentane (.035%), water (.0033%). |
| EPTC | 2–6 | Miscible in acetone, ethyl alcohol, kerosene, methyl isobutyl ketone, and xylene. Only .037% in water. |
| Fluometuron | .8–4 | Soluble in dimethylformamide, acetone, ethanol, and isopropanol. Only .009% in water. |
| Trifluralin | .5–1 | >50% soluble w/v in acetone, acetonitrile, chloroform, dimethylformamide, dioxane, hexane, methyl ethyl ketone, and xylene. 44% soluble w/v in methyl cellosolve, and .00003% in water. Formulated with xylene, ethyl benzene, and naphthalene. |
| Insecticides: | | |
| Carbaryl | .5–2 | Soluble in most polar organic solvents such as acetone. Only .004% in water. |
| Cypermethrin | .025–.1 | Soluble in methanol, acetone, xylene, and methylene dichloride. Insoluble in water. |
| Lambda cyhalothrin | .025–.04 | Soluble in most organic solvents. Low solubility in water. Formulated with xylene based petroleum solvent. |
| Malathion | .9–2.5 | Soluble in most organic solvents. Only .0145% soluble in water. Formulated with xylene. |
| Permethrin | .05–.4 | Very soluble in most organic solvents except ethylene glycol. <.0001% soluble in water. |
| Piperonyl butoxide | .1–.8 | Soluble in most common organic solvents and petroleum distillates. Very slightly soluble in water. |
| Fungicides: | | |
| Chlorothalonil | .56–4.13 | Slightly soluble in organic solvents and insoluble in water. |
| Miscellaneous: | | |
| Dyes & stains | | Available in water soluble and solvent soluble forms. |

N-methyl pyrrolidone (NMP) is used as a solvent in some applications. NMP is neither highly flammable nor carcinogenic and should pose little or no problem with the Environmental Protection Agency.

Other solvents that may be used are acetone, 100% denatured anhydrous ethanol, methylene chloride, 95% ethanol, 95% denatured ethanol, dimethylformamide, and gamma butyrolactone, to name a few. In practice, the solvents used with the active agents are generally known in the agricultural industry. Each producer or deliverer of the active agents generally knows which solvents can be used with its active agent.

Although any active agent can be used, the preferred embodiment uses alachlor, alphamethrin, atrazine, benzocaine, carbaryl, chlorothalonil, cymiazole, cupric hydroxide, cypermethrin, EPTC, fluometuron, lambda cyhalothrin, permethrin, piperonyl butoxide, malathion, streptomycin, or trifluralin. This list is not intended to be comprehensive but merely illustrative.

The skilled artisan in the agricultural industry knows the effective amounts of a particular pesticide to be used to accomplish its purposes in terms of pounds of pesticide per acre (lb/A) for the particular crop. The particular organic solvent for a desired pesticide is also known. Table I shows the known effective agricultural use rates and solvents for Cymiazole and benzocaine are used as active agents topically applied to animals, and streptomycin is a bactericide used on fruit trees. In such agricultural applications, these pesticides are used in amounts measured in parts per million (ppm).

Cymiazole is an experimental insecticide, which is not registered in the United States. It is soluble to obtain an application amount of about 300 ppm of the solvent. It is 80% soluble in dichloromethane, 75% in methanol, 70% in toluene, 35% in octanol, 35% in NMP, 30% in isopropanol, 5% hexane, and 0.005% in water. It is formulated in an aromatic solvent.

Streptomycin is used in an amount of about 100 ppm of the liquid for its agricultural use and is water soluble. Streptomycin is not very soluble in organic solvents.

Benzocaine is used for various agricultural uses and in a particular application on animals, in combination with cymiazole. Generally, benzocaine is used in an amount of about 1,000 ppm of the solution being used and is very soluble in ethanol and ether. It is insoluble in water.

N-methyl pyrrolidone is an excellent general solvent. It dissolves most of the granulated plant lecithin constituents into it in the production of a NMP lecithin-containing stock solution. However, ethanol dissolves predominantly the phosphatidylcholine (PC) in the production of an ethanol lecithin-containing stock solution. The other N-methyl pyrrolidone soluble constituents in the N-methyl pyrrolidone stock solution may prevent N-methyl pyrrolidone from solubilizing PC to its capacity from the plant lecithin being used.

To overcome this problem, ethanol is first used to form a lecithin solution wherein the PC is extracted (solubilized) from the granulated or liquid lecithin into the lecithin solution. Then the ethanol is removed and the PC redissolved in the N-methyl pyrrolidone. This helps to raise the PC content in the NMP stock. The extraction method does not add much to the total cost of the production process, but has extremely high PC levels. The extraction process could be done on any of the lecithins (high or low grade), depending on the desired result. Less expensive (14% PC) lecithins may be used as opposed to the more expensive (50% PC) granular lecithin depending on the desired result.

In mixing the lecithin and the solvent together, the preferred embodiment calls for a w/v ratio of lecithin to solvent of 1:1 or 1:2, which is contrasted with the 1:3 as used in the prior art. This allows for the loading of high concentrations of AA into the stock, since it contains such high levels of PC.

The present process uses only one solvent in the formulation as a carrier for the lecithin and the AA. However, a "double solvent system" can be employed when certain active agents may not be soluble in a particular solvent that dissolves a considerable amount of lecithin. In this case, the AA may be dissolved in another solvent system, that may dissolve less lecithin but have a high capacity for the AA. The second solvent system may be used to dissolve the AA, while the addition to the first solvent system increases the amount of lecithin material into the solution, thereby ensuring the encapsulation of the AA. A double solvent system uses two, and the progression continues.

For each solvent system, the solvents are mixed with the lecithin before anything else. In a double solvent system, one will take two single solvent systems and mix them together. For example, for a double solvent system using solvents A and B, single solvent system A is produced when ethanol and a lecithin are mixed, and single solvent system B is produced when N-methyl pyrrolidone is mixed with a lecithin. The AA would be added to the solvent system that had the higher solubility level for that particular AA.

The amounts of each single solvent system mixed together to form a double, triple or multiple solvent system, would vary depending upon the AA and what the particular solvent systems were.

More than one AA in a formulation can necessitate a solution requiring a triple solvent system. The addition of bulking agents such as methyl cellulose or carbopol and other stabilizing agents required in some formulations could require a triple solvent system.

A large number of agricultural compounds degrade in the presence of ultraviolet light. The microencapsulation protects any AA enclosed within from the environment and ultraviolet light. Carotenoids are natural pigments that act as ultraviolet filters and are present in the lecithin material purchased from the manufacturer. High carotenoid concentrations are generally present in lecithin due to the lecithin extraction and refinement process.

The carotenoid concentration in the stock material may be regulated either by selective extraction or by total extraction from the lecithin material and then metering it back into the stock material. Regulating the carotenoid concentration would also regulate the rate of ultraviolet decomposition of the AA. Therefore, the length of time the AA will remain in the field can be controlled by the amount of the carotenoids in the lecithin.

Placement of a large amount of carotenoid in the system can protect the AA in the field for an extended period of time. Controlling the rate of release and breakdown of the encapsulated AA in this manner will also reduce the possible acute toxic effects when applied to crops or animals.

Depending on the AA used and its desired concentration in the final formulation, the PC content in the stock material may be selected for the AA by simple extraction techniques from less expensive lecithin materials with lower PC concentrations. The desired concentration of the AA in the final formulation is determined in accordance with the particular agricultural use rate established for the active agent such as the pesticides in Table I.

In accordance with the invention, first the organic solvent is selected to carry the necessary amounts of active agent to produce the required agricultural use rate in the final formulation of the encapsulated active agent. At the same time, the organic solvent selected for the active agent must dissolve an effective amount of plant lecithin in solution to provide an intermediate active agent solution having a sufficient PC content for producing the vesicle formation of the liposomal encapsulation when the intermediate active agent solution is mixed with water.

Unlike the prior art, the most expensive lecithin is not required. Lecithin comes in different grades, depending upon the percentages of the components with phosphatidylcholine as the most important component. The higher the concentration of PC in the lecithin, the better the lecithin and the more expensive the process. Depending upon the active agent, the present method uses between five (5) to fifty (50) percent and, more particularly, fourteen (14) to fifty (50) percent PC lecithin.

The present invention can use a "batch" process to produce its stock solution. The production of the stock solutions under the present process may be automated to eliminate the slowness of the batch process. In doing so, the present invention utilizes augers and centrifuges to achieve the desired automation.

A system of a specific embodiment utilizes an auger to mix the lecithin and the solvent. As the mixing takes place the materials are moved down the auger leaving room for the addition of new unmixed materials on an automatically metered basis. As the materials become thoroughly mixed they are emptied into centrifuges for separation.

The centrifuges operate on a rotational basis. The rate of rotational speed of the centrifuges coincides with the flow rate of the auger and is designed to produce little or no backup in the system. The materials separated in the centrifuges are pumped into separate tanks for storage and disposal. Other processes such as those used in the alcohol distillery industry could also be utilized.

Due to the low flash point of ethanol and its extreme flammability all drive mechanisms for the system must be air-driven. The use of this technique in other industrial applications using ethanol has proven to be the most economic approach as opposed to providing a totally explosion proof electrical system. All compressors and other equipment for the pneumatic system would be located in other rooms or buildings away from the production area. The compressed air would be piped to each location.

Although any active agent can be used, in the preferred embodiment, the following active agents are used: pesticidal boron, alachlor, alphamethrin, atrazine, benzocaine, carbaryl, chlorothalonil, cymiazole, cupric hydroxide, cypermethrin, dyes, EPTC, fluometuron, lambda cyhalothrin, malathion, permethrin, piperonyl butoxide, stains, streptomycin, and trifluralin.

Although any organic solvent can be used, in the preferred embodiment, the following organic solvents are used: ethylene glycol, acetone, 100% denatured ethanol, 95% denatured anhydrous ethanol, dimethylformamide, gamma butyrolactone, methylene chloride, and N-methyl pyrrolidone.

In the preferred embodiment, the lecithin is selected from a group consisting of soybean oil, cottonseed oil, canola oil, wheat oil, kelp, peanuts, and sunflower seeds. The lecithin form is selected from a group consisting of liquid, granular, powder, gel, and paste. The lecithin has a PC content ranging from, but not limited to, 5% to 50% in the preferred embodiment. The PC content may be achieved by direct extraction, commercial preparation or custom blending.

Although any carotenoid content may be used, the preferred embodiment uses a carotenoid content from between substantially 0 to 1 percent to avoid active agent buildup. The carotenoid content may be achieved by direct extraction, commercial preparation or custom blending.

Commercially available plant lecithin is composed of the phospholipids phosphatidylcholine (PC), phosphatidylethanolamine (PE), phosphatidylinositol (PI), and phosphatidic acid (PA), carotenoids, and, depending on the grade, varying levels of oils, triglycerides, fibrous materials and, in some cases, additives and surfactants. Commercial lecithin is available in dry granular, liquid, gel, paste, and powder forms.

A solvent is selected for a particular stock material from available solvents that will dissolve the active agent and a compatible grade of lecithin and also be soluble in water. Different forms of plant lecithin (i.e. dry granular, liquid, gel, paste, and powder) have different levels of solubility in certain solvents. The form of lecithin chosen is thus dependent upon the solvent required to dissolve the active agent. For instance, if an active agent is soluble in ethanol then a lecithin form with low oil content such as a dry granular or gel would be selected because oily liquid lecithin forms are not very soluble in ethanol.

Flocculation problems sometimes arise when mixing with water due to an incompatibility of the solvent-active agent-lecithin form mixture. To overcome this problem, solvents and lecithin forms must be substituted with others to find the best combination for optimum suspensions in water. Also, when there is an active agent that is only soluble in hydrophobic nonpolar solvents, a co-solvent that is miscible in water and the nonpolar solvent must be introduced into the solvent system in order to mix with water.

Since lecithin is made up of many components, dissolving lecithin regardless of its form in a solvent will dissolve some of the components other than PC as well.

Specific examples of the invention are as follows:

EXAMPLE I

An industry available liquid lecithin was mixed with N-methyl pyrrolidone (NMP) in a 1:2 v/v ratio. This mixture was stirred until it became visibly homogenized. It was then poured into a separatory funnel and allowed to settle. After sufficient time for settling took place (24–48 hr.), the bottom sludge fraction was drawn off and discarded while the top portion was decanted and saved as usable stock material.

This stock material is the primary carrier system for chlorothalonil, the active agent to be added. The following formulation (designated ATX-6301) of one gallon provides an optimum suspension with minimal rapid settling when ultimately added to water to effect encapsulation.

| | |
|---|---|
| Chlorothalonil technical (98% purity) | 0.90 lbs |
| Anti-microbial agent | 0.29 ozs (0.24 fl. oz.) |
| Anti-foaming agent | 0.14 ozs (0.14 fl. oz.) |
| Thickening agent | 1.43 ozs |
| Stock material | 7.90 lbs (0.83 gal.) |

Materials mixed with the concentrate add to stability and efficacy of the entire system. The anti-microbial agent retards bacterial decomposition of chlorothalonil when applied to the field. The anti-foaming agent is added because the stock material has a tendency to foam when agitated which would hamper the concentration's ability to be accurately measured out for field application. Due to chlorothalonil's insolubility, it settles out in the concentrate rapidly which necessitates the need for a thickening or suspending agent. The thickening agent is to be dispensed accurately.

A rate of 1.5 lb chlorothalonil is required to spray an acre of tomatoes to control various fungal diseases. To accomplish this using the chlorothalonil concentrate of the invention, 1.7 gal of the concentrate was added to a water in a spray tank previously calibrated, according to standard practice, to deliver 20–40 gallons of finished aqueous spray solution to the acre.

Liposome formation is caused when the concentrate comes into contact with the water in spray tank. With the chlorothalonil microencapsulated according to the invention, the longevity of the pesticide is extended so that it does not have to be applied as often as other chlorothalonil products. Other new and unexpected results such as a significant increase in crop harvest have been obtained using the procedure of this invention in the field as discussed below.

EXAMPLE II

An agricultural industry available dry granular or powder lecithin was mixed with absolute ethanol in a 1:2 w/v ratio and agitated until all the lecithin was dissolved in the solvent. (For safety concerns, it is not recommended to heat mixtures for enhancing the dissolving of the solid material in volatile organic solvents such as ethanol.)

After all the lecithin dissolved, the mixture was transferred to a separatory funnel and allowed to settle. After sufficient settling time, the bottom sludge layer was drawn off and discarded and the top fraction saved as usable stock material. Formulation ATX-1201 comprises:

| | |
|---|---|
| Permethrin technical (92% purity) | 1.02 lb |
| Stock material | 6.48 lb (0.9 gal) |

An average rate of 0.2 lb permethrin per acre is usually required to control most insect problems in a variety of cropping situations. To accomplish this, 1.7 pints permethrin concentrate of the invention was added to a previously calibrated spray tank, according to standard practice, to deliver 20–40 gal of finished aqueous spray solution to the acre.

Here again, liposome formation is caused when the concentrate comes into contact with the water in the spray tank. By microencapsulating, the effective longevity of permethrin with its other unique features produce new and unexpected results in the field as discussed below.

EXAMPLE III

The stock material for streptomycin was made in the same manner as for permethrin using a 1:2 w/v ratio of lecithin to solvent. A 25% w/v streptomycin concentrate (ATX-1301) was formulated to control fireblight in apples. A gallon of streptomycin concentrate was made by bringing 2.09 lb of streptomycin sulfate up to a gallon with stock material. The recommended rate to control fireblight in fruit trees is to prepare a 100 parts per million streptomycin spray solution. Thus, 5.1 fl. oz. of the streptomycin concentrate of the invention was added to 100 gallons of water in a calibrated air-blast orchard sprayer. On the average, this volume of spray solution will cover approximately an acre of fruit trees. Field test results for ATX-1301 are discussed below.

EXAMPLE IV

The components of a borate insecticide concentrate made in accordance with the invention includes the following percentages by weight:

1. 20.29% disodium octaborate tetrahydrate material having 98.6% purity,
2. 52.71% ethylene glycol,
3. 20.34% liquid lecithin having at least 57% acetone insolubles,
4. 6.66% of poly(oxy-1,2-ethanedlyl)-alpha-(nonylphenyl)omega-hydroxy surfactant.

The apparatus used to make the concentrate is commercially available and requires little or no fabrication or alteration. The ethylene glycol and surfactant are added to a heated vat with agitation. Liquid lecithin is then introduced with agitation until the solution is homogenized. The vat is heated to approximately 300° F. being careful not to exceed the boiling point of ethylene glycol or the surfactant so that there are no vapors boiling off. The disodium octaborate tetrahydrate is then added with agitation. The heat and agitation of the solution is maintained until all of the disodium octaborate tetrahydrate is dissolved. The resulting concentrate can be pumped into the desired containers while still warm and the viscosity less. The final product is designated ATX-9101 and contains 2 lb of disodium octaborate tetrahydrate for each gallon of boron-containing concentrate.

The following additional boron-containing compounds may be adapted to the formulations of this invention.

| | |
|---|---|
| Boric oxide in the form of boron trioxide or anhydrous boric acid) | $B_2O_3$ |
| Borax | $Na_2B_4O_7$—$10H_2O$ |
| Borax 5 mol - borax pentahydrate | $Na_2B_4O_2$—$5H_2O$ |
| Boric acid | $H_3BO_3$ |
| Sodium metaborate 4 mol | $Na_2B_2O_4$—$8H_2O$ |
| Sodium perborate | $NaBO_2$—$4H_2O$ |
| Potassium tetraborate | $K_2B_4O_7$—$4H_2O$ |
| Potassium pentaborate | $K_2B_{10}O_{14}$—$8H_2O$ |
| Ammonium biborate | $(NH_4)_2B_4O_2$—$4H_2O$ |
| Ammonium pentaborate | $(NH_4)_2B_{10}O_{14}$—$8H_2O$ |

Other boron-containing pesticidal materials may be used in accord with this invention and include metaboric acid, sodium borate, disodium octaborate, disodium octaborate tetrahydrate, boron trioxide, anhydrous boric acid, borax decahydrate, a mixture of borax and boric acid, sodium tetraborate pentahydrate, sodium pentaborate, sodium pentaborate with anhydrous borax, an organometallic compound of boron, calcium boride, ulextile, colemanite, barium triborate, or calcium triborate.

The encapsulated borate formulation of the invention (ATX-9101) is produced by an encapsulator process that allows boric acid to be used under agricultural conditions when a nonencapsulated boron-containing material is otherwise unable to be so used. ATX-9101 is the first liquid boric acid product that is effective in controlling agricultural insect pests, namely, alfalfa weevil (*Hypera poslica* Gyllenhal), corn ear worm (*Heliothis zea* Boddie), cabbage looper (*Trichoplusia ni* Hubner), imported cabbage worm (*Pieris rapae* L.), cross striped cabbage worm (*Evergetis rimosalis* Guenee), cotton aphid (*Aphis gossypii* Glover), gypsy moth (*Porthetria dispar* L.), cotton thrip (*Frankliniella sp.*), and tobacco flea beetle (*Epitrix hirtipennis* Melsheimer). Under agricultural conditions, ATX-9101 has maintained the high level of pesticidal efficacy for boron that it has always had in non-agricultural conditions.

New and Unexpected Results

Although liposomal encapsulation is found in the pharmaceutical field and in the household pesticide field, nothing in the prior art suggests, teaches, or discloses that a liposomal encapsulated agricultural active agent such as a pesticide will adhere to the organic faction of soil and thereby greatly reduce and/or substantially eliminate surface run-off of the encapsulated agricultural active agent or the leaching of the liposomal encapsulated agricultural active agent through the soil into the submerged aquafer. Moreover, adherence to the soil organic faction retards and in some instances may substantially preclude volatilization of agricultural pesticides in the field.

The agricultural formulations of the invention provide natural long term benefits for the active agricultural pesticide. The long term effect of the encapsulated agricultural formulation comes from both diffusion and their natural breakdown. Nothing in the prior art related to liposomal encapsulation of any material suggests, teaches, or discloses that a liposomal encapsulated agricultural chemical will adhere to plants to which it is applied and thereby substantially precludes run-off of the chemical from the plants in the field.

Unlike other known encapsulation techniques that include polyvinylchloride, polyurea and polymerization encapsultors, the encapsulated agricultural pesticides of the invention applied to crops in the fields unexpectedly do not leave an insoluble residue on the plants and in the soil. Thus, the formulations of the invention unexpectedly provide positive environmental aspects to agricultural chemical active agents such as pesticides in farming.

The known agricultural chemicals are enhanced in their effectiveness to such a degree with the formulations of the invention that, instead of having to apply them weekly as required now for effectiveness in the field, the same pesticidal effectiveness is obtained by applying the same required amounts once every other week or every third week. Consequently, the use of agricultural pesticides may be reduced by at least 50% without losing their pesticidal effectiveness in agricultural applications.

The liposomal encapsulated agricultural pesticides are unexpectedly much safer to handle because the encapsulation materials do not adversely effect the human being and/or animals if they come in contact with the skin and/or other body surface. And the agricultural pesticides formulated according to the invention do not necessarily require the "inert ingredients" presently used in existing agricultural chemical formulations throughout the world.

Moreover, the level of carotenoid in the lecithin-containing solution formulations of the invention can be regulated to control the ultraviolet (UV) barrier characteristics of the liposomal encapsulated agricultural pesticides thereby enhancing their pesticidal effectiveness in farming applications. Thus, the natural composition of the unique pesticide formulation of the invention provides an excellent protective barrier from UV radiation and enhances the active life of UV degradable compounds.

Safety

The agricultural solvent solution formulations of the invention do not require specialized storage conditions because they may be stored at room temperature for the duration of the product shelf life.

Enhancement in the Soil

The composition and nature of the agricultural formulations of the invention provides protection from immediate microbial breakdown, better coverage of the foliage, and better adhesion to plant cuticular waxes thereby preventing removal due to rain or irrigation.

Since less active ingredient may be used with the unique product of the invention because unexpectedly fewer field applications are required, potentially lower residue levels of agricultural pesticide should be found in the plant tissue.

Leaching and Pesticidal Activity Evaluation of Atrazine, an Agricultural Herbicide Atrazine formulated according to the invention has been evaluated under two different "worse case" scenarios to prove its ability to reduce the leaching of atrazine in different soils while maintaining its pesticidal efficacy, i.e., its ability to kill weeds.

Leaching tests of agricultural pesticides are commonly made in a soil column. A tubular container defines a column about 12 inches long and is filled with the soil in which the pesticide is to be tested. The surface area at the top of the column is first calculated and based on that, the amount of material to be sprayed on the top surface area corresponds to amounts generally used in known field applications.

The pesticide is sprayed on the top surface area of soil in the column. Water is then applied to the column and allowed to run through the column. Soil samples at one inch increments down the column are placed in pots and planted with weed seeds disposed therein. Thus, the pesticidal efficacy is determined at any particular level by counting the number of weed seeds that germinate in each pot.

During the first evaluation, ATX-6103 (Atrazine formulated according to the invention) and Atrazine 4L (a product presently being used in field applications) were respectively applied to soil columns containing Myakka sand at 3.36 kg/ha. Approximately 15 cm of water equivalent to 6 inches rainfall were applied to each column and allowed to drain for 24 hours. Velvetleaf (common weed) was seeded into the soil of the columns for determination of the efficacy of the pesticide materials.

The formulated atrazine (ATX-6103) according to the invention had equal or better control of the velvetleaf as the Atrazine 4L. The results, therefore, show that the atrazine formulation of the invention did not change its ability to kill weeds.

As anticipated with respect to leaching in the Myakka sand columns, the leaching of the ATX-6103 and Atrazine 4L was the same. This is due to (1) the extremely low cationic exchange capacity of sand, (2) lower adsorptive surface area compared to soils containing higher clay contents, and (3) little or no organic matter present.

In the second leaching evaluation, ATX-6103 and Atrazine 4L were applied at 11.2 kg/ha to soil columns containing an Etowah silt loam with 1.4% organic matter, pH of 5.5 and % sand/silt/clay of 29/52/19. Approximately 15 cm of water were applied to the columns, which were then allowed to drain for 12 hours. Atrazine residues in column sections were analyzed using High-Performance Liquid Chromatography (HPLC) with a UV detector.

The ATX-6103 formulation dramatically and unexpectedly reduced the leaching of atrazine by retaining approximately 50% of the applied material in the top 6 inches of the soil. This proves that even under "worse case" conditions (5×application rate, wet soil+2 pore volumes) in an agronomic soil, the formulation of the invention successfully increased the amount of atrazine contained in the surface soil zone compared to the commercial Atrazine 4L.

Field Evaluation of Streptomycin, an Agricultural Bactericide

Fireblight is a major bacterial disease problem in apples and pears nationally. In 1987, Tennessee lost over 30% of its apple crop to fireblight estimating over five hundred thousand dollars ($500,000) in lost revenue. Tennessee is not even ranked in the top 30 apple producing states in the U.S.

Streptomycin, an agricultural bactericide, is the best commercially available control for fireblight but breaks down rapidly in sunlight. During spring months when rainfall is prevalent, agricultural streptomycin as well as other agricultural compounds are washed from the tree before adequate pest control can be obtained.

The objective of the evaluation of this streptomycin formulation of the invention was to prove that one application of the formulated agricultural streptomycin (ATX-1301) provided superior fireblight control compared to multiple applications of the available commercial streptomycin now used for agricultural applications.

To ensure adequate potential infection, the fireblight susceptible apple variety 'Cortland' was used for this evaluation. Oversight of this evaluation was by the University of Tennessee and the private grower.

TABLE 1

Fireblight control in 'Cortland' apples with applications of 100 ppm solutions of commercial streptomycin and Applicants' formulated agricultural streptomycin at different stages of bloom in 1990.

| Treatment | No. of applications | Average no. of strikes* | Average severity of strikes** |
|---|---|---|---|
| Commercial*** | 6 | 7.2 | 10.0 |
| ATX-1301 @ 5% bloom | 1 | 6.0 | 9.6 |
| ATX-1301 @ 50% bloom | 1 | 5.7 | 6.6 |
| ATX-1301 @ 100% bloom | 1 | 8.0 | 8.2 |

*Strike denotes an individual fireblight occurrence.
**Rated on a scale of 1 (minor) to 10 (severe).
***Applied between 4/1/90–5/22/90.

Summary Regarding Applicants' Agricultural Streptomycin Formulation

The formulated streptomycin ATX-1301 of the invention applied at 50% bloom unexpectedly outperforms 6 consecutive applications of commercially available agricultural streptomycin.

The formulated streptomycin applied only once at 50% bloom surpassed the commercial streptomycin in the number of strikes per tree as well as the severity of strikes (Table 1).

During the 6 week evaluation period, 6.7 inches of rainfall were measured. These results proved that Applicants' formulated streptomycin did not wash off the leaves as did the commercial streptomycin formulation.

These positive new and unexpected factors will carry over to other agricultural compounds and other crops, reducing the need for multiple applications of agricultural pesticide during rainy weather.

Field Evaluation of Permethrin, an Agricultural Insecticide

Field evaluation compared the formulated permethrin (ATX-1201) of the invention under several different conditions. And the longevity and pesticidal efficacy of the formulated permethrin was compared to Pounce, a commercially available insecticide. The comparative analysis was with respect to the effectiveness of these two agricultural compounds on alfalfa weevil larvae. The percentage control was plotted along the 6 week period of pesticidal application. The commercially available Pounce starts off at about 90% insect control and then drops off drastically beginning the 5th week while the unique product of the invention holds strong at better than 50% insect control at 6 weeks. These figures constitute averages over 3 years at two different locations in alfalfa application.

There are several variables that will affect the results including the degree of infestation of the alfalfa weevil and how much rain occurs during the 6 weeks before the crop is cut.

The yield comparison of alfalfa between ATX-1201 and Pounce when applied equally on the alfalfa showed no difference in yield between the two products in 1990. But the formulated permethrin ATX-1201 produced higher yields in 1992. In other words, the yield effectiveness of permethrin was increased using the invention's formulation and constitutes new and unexpected results. By controlling the number of weevils in the alfalfa, the less damage there is to the crop.

The evaluation of the efficacy of the invention's permethrin involved applying it at a rate of 50% the frequency of the standard Pounce in 1990 and equally in 1991 with respect to cotton. The ATX-1201 showed less damaged squares of cotton and less infestation with half as much as being applied as the Pounce in 1990.

The comparative yield results in 1990 and 1991 show the invention's formulated permethrin exceeded the cotton lint yield of the standard with 50% frequency of application. The unexpected increased yield could represent a significant amount of product for the farming consumer.

The longevity and efficacy of the ATX-1201 of the invention compared to Pounce on Heliosis neonates in soybeans produced in this greenhouse study shows that the Heliosis (caterpillar) had 100% mortality for the first two weeks and began dropping off for the ATX-1201. The commercially available Pounce generally shows a lower pesticidal efficacy over the 5 weeks as applied.

Field Evaluation of Chlorothalonil, a Fungicide

The chlorothalonil product evaluation on tomatoes involved the invention's formulated chlorothalonil, (ATX-6301) and Bravo 720, a commercial name for a commercial grade chlorothalonil. The ATX-6301 agricultural formulation is simply the Bravo product formulated according to the invention.

The purpose of this study was to determine if chlorothalonil processed according to the invention could produce control after a single spray. On July 11 of the test year, 1.5 pounds of each of the two fungicides were applied to the crop. On July 17, 24, 30, and August 7, only the commercial Bravo was applied. By August 7 of the test year, seven pounds of Bravo were applied per acre.

On August 14, each of the two different fungicidal products was applied to the respective acreage again. By that date, Bravo had nine pounds per acre and the ATX-6301 formulation had three pounds per acre. By August 29, the ATX-6301 was applied in the amount of 4.5 pounds per acre and Bravo had been applied in the amount of 12 pounds per acre.

Early blight is a fungal disease that attacks tomatoes, including both the plant and the fruit. The worse it gets, the less the tomato plants do well and the quality of the fruit is significantly diminished. Unexpectedly, the test results showed that only three applications of the ATX-6301 product were required as compared to eight applications of the commercial Bravo. The pesticidal effectiveness of the respective products was measured extending from July 30 through September 3 of the test year. The test results support the idea that the application of the invention's ATX-6301 every other week produced a significantly better result than the results in 1991.

In 1992, Bravo was applied every week in two different applications. One bi-weekly and one weekly application of the invention's formulated agricultural chlorothalonil (ATX-6301) showed that the lesser applied liposomal encapsulated chlorothalonil of the invention produced substantially the same results as the Bravo product. Its bi-weekly application was just under the other two and dropped off significantly in the 6th week when no further application was made. Thus, using about ½ the amount of the invention's formulation unexpectedly produced substantially the same results as the existing commercially available product for the first 5 weeks.

In the 1991 field test, the late blight occurrence killed tomatoes involved in all of the testing. Consequently, no analysis was made of the respective yields associated with the test materials.

Tomatoes are rated by size. Number ones are the biggest and best. Number two tomatoes are the next best and culls are thrown out. The invention's formulated chlorothalonil had a slightly higher yield in both the number one and number two tomatoes showing a significant increase in the overall total. This represents an increase yield of about 4.5 tons per acre more in total yield. The yield was lower in 1992 because of the late blight. Thus, it is anticipated that instead of a bi-weekly application, during the period when late blight may occur, the frequency of application of the novel formulation would be increased to a weekly application.

The 1993 product evaluation showed that there were no significant differences in pesticidal efficacy between the compared test analysis including the bi-weekly application of the invention's liposomal encapsulated chlorothalonil product. The marketable yield increase in terms of percent change unexpectedly showed significant increases in product yield recorded with significant decrease in the culls both with the weekly and bi-weekly applied chlorothalonil formulation of the invention.

The increase in yields experienced with the ATX-6301 more than make up for the use of the differences in cost because of the fewer applications the ATX-6301 required to achieve the same results as the Bravo 720. There was an increase of $1,611.39 per acre over the yield produced using the commercial Bravo 720. In other words, the farmer can spend $100.00 more per acre to use the invention's product, but will make $1,600.00 more per acre. That is a significant new and unexpected return on one's additional investment.

The test results with the tomatoes show that the increased yield unexpectedly produces significantly more income to the farmer by using the invention's product regardless of whether it is less or more in value per gallon because of the amount of increased yield experienced in comparison with the commercially available pesticide.

Summary of Pesticidal Evaluations

The invention's formulated agricultural compounds unexpectedly have proven themselves superior to all other compounds tested in the foregoing evaluations. A variety of agricultural chemicals processed in accord with the invention have been used in a variety of cropping situations with very positive results. Unexpectedly, the formulation of the invention have extended the longevity of active ingredients as exhibited in the product evaluations providing for extended control of insect pests, weeds, and plant diseases with a reduced amount of applications.

Based on the product evaluations, initial indications are that normal precipitation does not wash off the invention's formulated agricultural compounds from plants. This is reflected by the superior effectiveness of single applications of their formulated streptomycin in apples and their formulated permethrin in alfalfa.

The invention's formulations dramatically and unexpectedly reduced leaching as displayed in the atrazine evaluation. The degradation of active ingredients by UV light was dramatically and unexpectedly reduced by formulation techniques. This was proven in every product evaluation conducted by the University of Tennessee.

There are numerous unexpected economic advantages to using the formulations of the invention. A reduction in the number of applications means less material a grower has to buy. The cost of pest control can be expensive. For example, it normally costs about $9.00 to treat an acre of cotton to control cotton bollworm with commercial cypermethrin. This figure is magnified significantly when the grower has to treat large acreages at weekly intervals.

More specifically, a grower treating 100 acres of cotton weekly for bollworm, for 6 weeks, would spend $5,400.00/year in materials. Based on our calculations there would be a 50% savings using the invention's formulation. This would amount to a $2,700.00 savings in materials alone on 100 acres of cotton. Based on the fact that there are 10 million acres of cotton grown in the United States there would be a 270 million dollar savings nationally each year. This would have significant positive economic effects.

These savings are in materials alone and will be increased when savings in other areas are added. The savings illustrated in this example are for one product on one crop. It is believed that these savings will be equally as dramatic on other crops in other areas.

While the agricultural pesticide formulations have been shown and described in detail, it is obvious that this invention is not to be considered as limited to the exact form disclosed, and that changes in detail and construction may be made therein within the scope of the invention without departing from the spirit thereof.

Having thus set forth and disclosed the nature of this invention, what is claimed is:

1. A prepackaged boron pesticide product comprising:

a) a pesticidal boron in sufficient amounts to destroy plant-eating insects when the prepackaged boron pesticide product is mixed and sprayed with water onto agricultural plant crops, b) said sufficient amounts of said pesticidal boron being mixed with a solution of an organic solvent having a saturation level amount of plant lecithin in solution forming said organic solvent solution containing no undissolved portion, c) said prepackaged boron pesticide product being effective to form a slow release boron pesticide composite formulation including a phospholipid material derived from said plant lecithin when mixed with water.

2. A boron product as defined in claim 1 wherein said organic solvent is ethylene glycol.

3. A boron product as defined in claim 1 wherein said organic solvent solution includes a surfactant.

4. A boron product as defined in claim 1 wherein said pesticidal boron is disodium octaborate tetrahydrate in an amount sufficient to form a concentration of about 2 pounds of disodium octaborate tetrahydrate being in solution in each gallon of said boron product.

5. A boron product as defined in claim 1 wherein said pesticidal boron is in a weight to weight ratio in the range of 500 parts per million to 2.5 pounds in each gallon of said boron product.

6. A boron product as defined in claim 1 wherein said pesticidal boron comprises an effective amount of an insecticidal boron based on elemental boron content of up to about 5.5% by weight.

7. An intermediate pesticidal boron formulation comprising:

a) a pesticidal boron in an effective amount sufficient to effect pesticidal activity when the pesticidal formulation is mixed and sprayed with water onto vegetation, b) said effective amount of pesticidal boron being mixed with an organic solvent solution having no undissolved portion and a saturation level amount of plant lecithin in solution to form a pesticidal solvent mixture, c) said pesticidal solvent mixture being effective to form a slow release boron pesticide composite comprising pesticidal boron liposomally encapsulated with a phospholipid material derived from said plant lecithin when said pesticidal solvent mixture is mixed with water.

8. A pesticidal formulation as defined in claim 7 wherein said pesticidal boron is boric oxide, metaboric acid, sodium borate, disodium octaborate, disodium octaborate tetrahydrate, boron trioxide, anhydrous boric acid, borax, borax pentahydrate, borax decahydrate, a mixture of borax and boric acid, boric acid, sodium metaborate, sodium perborate, sodium tetraborate pentahydrate, sodium pentaborate, sodium pentaborate with anhydrous borax, potassium tetraborate, potassium pentaborate, ammonium biborate, ammonium pentaborate, an organometallic compound of boron, calcium boride, ulextile, colemanite, barium triborate, or calcium triborate.

9. A pesticidal formulation as defined in claim 7 wherein said pesticidal boron is an alkali metal borate, an alkaline earth metal borate or an alkali metal borohydride.

10. A pesticidal formulation as defined in claim 7 wherein said organic solvent solution includes carotenoid in an amount sufficient to control the ultraviolet degradability of said slow release pesticide composite when said formulation is disposed on said vegetation.

11. A pesticidal formulation as defined in claim 7 wherein said pesticidal solvent mixture includes ethylene glycol.

12. A pesticidal formulation as defined in claim 7 wherein said plant lecithin is derived from soybean oil, cottonseed oil, canola oil, wheat oil, kelp, peanut oil, or sunflower seed oil.

13. A pesticidal formulation as defined in claim 7 wherein said plant lecithin has a phosphatidylcholine content in the range of from about 5% to about 50% by weight.

14. A pesticidal formulation as defined in claim 7 wherein said pesticidal boron is a borate.

15. A method for controlling the growth of or destroying agricultural pests comprising weeds, insects, fungi, and bacteria, said method comprising the step of bringing into contact with the agricultural pests an effective amount of the pesticidal boron formulation of claim 7 mixed with water to control the growth of or destroy agricultural pests.

* * * * *